United States Patent [19]
Kiyoura

[11] Patent Number: 4,599,446
[45] Date of Patent: Jul. 8, 1986

[54] PROCESS FOR THE PREPARATION OF 2-KETO-L-GULONIC ACID

[75] Inventor: Tadamitsu Kiyoura, Kamakura, Japan

[73] Assignee: Mitsui Toatsu Chemicals, Incorporated, Japan

[21] Appl. No.: 723,800

[22] Filed: Apr. 17, 1985

Related U.S. Application Data

[63] Continuation of Ser. No. 539,737, Oct. 6, 1983, abandoned.

[51] Int. Cl.$^4$ .................. C07C 51/235; C07C 59/215
[52] U.S. Cl. ..................................... 562/527; 562/577
[58] Field of Search ........................ 562/527, 538, 577

[56] References Cited

U.S. PATENT DOCUMENTS 2,190,377  2/1940  Dalmer et al. ...................... 562/527

FOREIGN PATENT DOCUMENTS 2903388  9/1979  Fed. Rep. of Germany ...... 562/527
85767  11/1971  German Democratic Rep. .................................... 562/538

OTHER PUBLICATIONS

Berkman et al., Catalysis Inorganic and Organic Reinhold Publishing Corp., New York, 1940, pp. 394–397.

*Primary Examiner*—Vivian Garner
*Attorney, Agent, or Firm*—McGlew and Tuttle

[57] ABSTRACT

A process for the preparation of 2-keto-L-gulonic acid by the oxidation of L-sorbose with an oxygen-containing gas in water used as the solvent, wherein the reaction is carried out in the presence of a specific catalyst, preferably with the pH of the reaction fluid kept within the range of 6 to 10. The catalyst contains platinum and/or palladium, as well as lead or bismuth. 2-Keto-L-gulonic acid is a compound which is useful as a precursor of vitamin C.

8 Claims, No Drawings

PROCESS FOR THE PREPARATION OF 2-KETO-L-GULONIC ACID

This is a continuation of application Ser. No. 539,737, filed Oct. 6, 1983, now abandoned.

BACKGROUND OF THE INVENTION

1. Field of the Invention

This invention relates to an improved process for the preparation of 2-keto-L-gulonic acid by the direct oxidation of L-sorbose.

2. Description of the Prior Art

In current processes for preparing 2-keto-L-gulonic acid by the oxidation of L-sorbose, hypochlorites, permanganates and the like are used as oxidizing agents. These oxidizing agents fail to selectively oxidize the —$CH_2OH$ groups of L-sorbose. Accordingly, it is necessary to react L-sorbose with acetone, prior to its oxidiation, and thereby protect the —$CH_2OH$ groups other than that situated in the C-1 position.

However, the above-described prior art processes have the disadvantages of using expensive oxidizing agents, involving multiple reaction steps, requiring troublesome procedures (e.g., for separating the by-product monoacetone-L-sorbose from diacetone-L-sorbose and recycling it), and consuming large amounts of secondary materials and energy.

In order to overcome these disadvantages, attempts have long been made to air-oxidize unacetonized L-sorbose in the presence of a noble metal catalyst. For example, U.S. Pat. No. 2,190,377 (1940) discloses a process in which L-sorbose is air-oxidized in the presence of a platinum/carbon powder catalyst to obtain 2-keto-L-gulonic acid in a 60% yield. However, this process requires a reaction time of as long as about 60 hours and fails to attain a satisfactorily high yield, thus leaving much room for improvement.

SUMMARY OF THE INVENTION

It is an object of the present invention to provide a process for the preparation of 2-keto-L-gulonic acid by the direct oxidation of L-sorbose which gives a high yield of 2-keto-L-gulonic acid after a short reaction time and, therefore, has great industrial advantages.

As a result of close investigation on the air oxidation of L-sorbose, especially on various catalysts useful for this purpose, the present inventors have discovered a catalyst which can oxidize L-sorbose efficiently in water used as the solvent and can greatly shorten the time required for the reaction, as compared with prior art processes. The catalyst used in the process of the present invention contains platinum and/or palladium, as well as lead or bismuth. Among conventional catalysts comprising a noble metal catalyst having a base metal (such as lead or the like) added thereto, the "Lindlar" catalyst, or a catalyst which reduces acetylenic bonds to olefinic bonds but does not change olefinic bonds to paraffinic bonds, is well known. In the case of the Lindlar catalyst, the noble metal catalyst is poisoned with lead to decrease its activity to some extent and thereby increase its selectivity. As described above, the catalyst of the present invention comprises a noble metal having lead or bismuth added thereto, but the resulting activity and reaction rate are greatly enhanced as compared with a catalyst comprising the noble metal alone. This clearly indicates that the mechanism of action of lead or bismuth in the catalyst of the present invention differs from that of lead in the Lindlar catalyst.

According to the process of the present invention, the necessity of preliminarily reacting L-sorbose with acetone to form diacetone-L-sorbose is eliminated and the reaction can be effected in a single step as contrasted with the prior art processes requiring three steps. Moreover, neither expensive oxidizing agents (such as hypochlorites and permanganates) nor additional steps for the disposal of the wasted oxidizing agent are required. Thus, the process of the present invention makes it possible to produce 2-keto-L-gulonic acid with industrial advantages.

DETAILED DESCRIPTION OF THE INVENTION

The catalyst used in the process of the present invention contains platinum and/or palladium, as well as lead or bismuth. Usually, this catalyst is supported on a suitable carrier such as activated carbon or the like. The platinum and/or palladium contained therein may be present in the metallic state or in the form of oxides, while the lead or bismuth may be present in the metallic state or in the form of hydroxides, oxides, chlorides, carbonates, basic carbonates, organic acid salts, nitrates, sulfates, phosphates or the like.

For use in the process of the present invention, the above-described catalytic material is supported on a suitable carrier such as activated carbon, alumina or the like. The amount of noble metal or metals supported on the carrier may range from 0.5 to 15% by weight and preferably from 1 to 10% by weight, while the amount of lead or bismuth supported thereon may range from 0.1 to 10% by weight and preferably from 0.5 to 8% by weight.

The catalyst may be prepared according to any conventional method. This can be done, for example, by soaking activated carbon in an aqueous solution of chloroplatinic acid and lead nitrate, alkalifying the solution by the addition of an alkaline substance (such as sodium carbonate or the like), and then reducing the metallic compounds with formalin. The most convenient method is to purchase a commercial catalyst comprising a noble metal supported on carbon powder and soak it in an aqueous solution containing a salt of lead or bismuth. Alternatively, the oxidation of L-sorbose and the preparation of the catalyst may be simultaneously carried out by adding a noble metal catalyst and a water-soluble salt of lead or bismuth to the water used as the solvent.

The process of the present invention is carried out in a solvent and water is used as the solvent. The raw material, or L-sorbose, is added to the water used as the solvent in such an amount as to give a concentration of 1 to 15% by weight and preferably 2 to 10% by weight. If the concentration of L-sorbose is higher than the above-described range, the reaction rate is reduced and the formation of by-products is increased, while if the concentration is lower than the above-described range, a large amount of energy is consumed for separating the product from the solvent after completion of the reaction.

In the case of batch operation, for example, the supported catalyst is usually used in an amount of 10 to 100 g per liter of the reaction fluid containing L-sorbose in the above-described concentration. The amount of catalyst used exerts an influence on the reaction rate. If the amount of catalyst used is too small, the time required for the reaction is prolonged and side reactions are increased, while if the amount of catalyst used is too large, the reaction rate is enhanced to shorten the time required for the reaction, but the cost of the catalyst becomes disadvantageously high. Thus, it is preferable to determine the optimum amount of catalyst used experimentally, depending on the particular reaction procedure and conditions.

The oxidizing agent used in the present invention is molecular oxygen. Although oxygen gas and air can be used, air is preferred in usual cases. The pressure of the oxygen-containing gas may range from subatmospheric pressure to 10 kg/cm$^2$.

Preferably, the reaction fluid is stirred and the oxygen-containing gas is blown therethrough so as to maintain intimate mixing and contact of the oxygen-containing gas, the reaction fluid and the catalyst which constitute the gaseous, liquid and solid phases, respectively.

As the reaction proceeds, the pH of the reaction fluid shifts from the vicinity of neutrality to an acid region because of the desired product resulting from the oxidation of L-sorbose. Since the oxidation slows down when the pH of the reaction fluid is in an acid region, it is preferable to keep the pH of the reaction fluid in the vicinity of neutrality or in a weakly alkaline region. For this purpose, an alkaline substance is added to the reaction fluid synchronously with the progress of the reaction so that the pH of the reaction fluid may be kept within the range of 6 to 10.

Useful alkaline substances include alkali metal hydroxides such as sodium hydroxide, potassium hydroxide, etc.; alkali metal carbonates or bicarbonates such as sodium carbonate, potassium carbonate, etc.; alkali metal salts of organic acids such as sodium acetate, etc.; alkali metal phosphates; and the like. Usually, an aqueous solution of such an alkaline substance is added to the reaction fluid by means of a constant delivery pump synchronized with a pH controller.

If the pH of the reaction fluid exceeds 10, the oxidation speeds up, but the formation of by-products is undesirably increased to lower the yield of the desired product. For that reason, the reaction should preferably be carried out with the pH of the reaction fluid kept within the range of 6 to 10 and more preferably 6 to 8.

The reaction temperature may range from room temperature to 70° C. and preferably from room temperature to 55° C.

In the case of batch operation, for example, the time required for the reaction generally ranges from 1 to 10 hours and usually from 1 to 6 hours.

In carrying out the process of the present invention, a stirred-tank reactor using a suspended bed of the complete-mixing type or a bubble-tower reactor is commonly employed. Alternatively, a fixed-bed reactor using a granular catalyst may also be employed. Both single- and multiple-stage reactors can be used in a similar manner.

After completion of the reaction, the reaction fluid from which the catalyst has been removed by filtration is concentrated under reduced pressure. Then, a water-soluble organic solvent (such as isopropyl alcohol or the like) is added thereto with vigorous stirring, so that the desired product precipitates as an alkali metal salt.

The 2-keto-L-gulonic acid prepared by the process of the present invention is a compound which is very useful as a precursor of ascorbic acid (vitamin C).

The present invention is further illustrated by the following examples.

EXAMPLE 1

A cylindrical stainless steel vessel having an internal diameter of 20 cm and fitted with baffle plates, a turbine-blade agitator and an air inlet tube was used as the reactor. One liter of a 6 wt. % aqueous solution of L-sorbose and 25 g of a catalyst comprising 5 wt. % Pt and 3 wt. % PbCO$_3$ supported on activated carbon powder were charged into the reactor, which was externally heated to 40° C. in a water bath. While air under atmospheric pressure was being blown into the reactor at a rate of 200 ml/min., the reaction was carried out with stirring at 500 rpm. As the reaction proceeded, an aqueous solution of sodium carbonate was successively added to the reaction fluid so that its pH might be kept within the range of 7 to 8. 2.5 hours after the commencement of the reaction, the alkali consumption became equivalent to the amount of L-sorbose used and the reaction was discontinued.

After completion of the reaction, the reaction fluid from which the catalyst had been removed by filtration was analyzed by high-speed liquid chromatography. Moreover, when the amount of 2-keto-L-gulonic acid salt formed was iodometrically determined according to the procedure described in Ann. Chem. Liebigs, 558, 171–177 (1947), it was found that 2-keto-L-gulonic acid sodium salt was obtained in an 87 wt. % yield.

EXAMPLES 2–4

The procedure of Example 1 was repeated using several different catalysts. The results thus obtained are summarized in the following table.

| Example No. | Catalyst | Time required for reaction (hrs) | Yield (wt. %) |
| --- | --- | --- | --- |
| 2 | 5% Pd, 3% Bi$_2$O$_3$/carbon powder | 4.5 | 77 |
| 3 | 3% Pd, 1% Pt, 2% Pb(OH)$_2$/carbon powder | 3.5 | 80 |
| 4 | 4% Pt, 1% Pd, 3% Bi$_2$O$_3$ carbon powder | 2.8 | 82 |

What is claimed is:

1. A process for the preparation of 2-keto-L-gulonic acid which comprises oxidizing L-sorbose with an oxygen-containing gas in water used as the solvent and in the presence of a carrier supported catalyst containing, based on the weight of the carrier, 1–10% of platinum and/or palladium and 0.5–8% of lead or bismuth, the reaction being carried out with the pH of the reaction fluid kept within the range of 6 to 8.

2. A process as claimed in claim 1 wherein the catalyst is carried on activated carbon.

3. A process as claimed in claim 1 wherein the oxygen-containing gas is air.

4. A process as claimed in claim 1 wherein the L-sorbose is added to the solvent in an amount to give a concentration of 1 to 15% by weight.

5. A process as claimed in claim 1 wherein the reaction temperature ranges from room temperature to 70° C.

6. A process for the preparation of 2-keto-L-gulonic acid which comprises contacting an aqueous solution containing 1–15% by weight of L-sorbose with an oxygen-containing gas in the presence of 10 to 100 grams per liter of reaction fluid of a carrier-supported catalyst containing platinum and/or palladium, and lead or bismuth for a period of 1–10 hours, while maintaining the pH of the reaction fluid within the range of 6 to 8, thereby oxidizing the L-sorbose into 2-keto-L-gulonic acid, the amount of platinum and/or palladium ranging from 1 to 10% by weight and the amount of lead or bismuth ranging from 0.5 to 8% by weight.

7. The process of claimed in claim 6, wherein the reaction is conducted for a period of from 1 to 6 hours.

8. The process as claimed in claim 7, wherein the reaction is conducted at a temperature from room temperature to 70° C.

* * * * *